US007902392B2

(12) United States Patent
Ochs et al.

(10) Patent No.: US 7,902,392 B2
(45) Date of Patent: Mar. 8, 2011

(54) METHOD FOR THE PRODUCTION OF ORGANOSILICON COMPOUNDS COMPRISING CARBOXY RADICALS

(75) Inventors: Christian Ochs, Burghausen (DE); Elke Fritz-Langhals, Ottobrunn (DE)

(73) Assignee: Wacker Chemie AG, Munich (DE)

( * ) Notice: Subject to any disclaimer, the term of this patent is extended or adjusted under 35 U.S.C. 154(b) by 1118 days.

(21) Appl. No.: 11/568,050

(22) PCT Filed: Apr. 11, 2005

(86) PCT No.: PCT/EP2005/051588
§ 371 (c)(1),
(2), (4) Date: Oct. 18, 2006

(87) PCT Pub. No.: WO2005/103060
PCT Pub. Date: Nov. 3, 2005

(65) Prior Publication Data
US 2009/0221842 A1  Sep. 3, 2009

(30) Foreign Application Priority Data

Apr. 21, 2004  (DE) .......... 10 2004 019 376

(51) Int. Cl.
*C07F 7/04* (2006.01)
*C07F 7/08* (2006.01)
(52) U.S. Cl. ........................... 556/439; 205/420
(58) Field of Classification Search .............. None
See application file for complete search history.

(56) References Cited

U.S. PATENT DOCUMENTS

| | | | |
|---|---|---|---|
| 2,763,675 A | 9/1956 | Porchaska et al. | |
| 2,875,177 A | 2/1959 | Bluestein et al. | |
| 2,900,363 A | 8/1959 | Bluestein et al. | |
| 2,957,899 A | 10/1960 | Black et al. | |
| 3,143,524 A | 8/1964 | Cooper et al. | |
| 3,391,177 A | 7/1968 | Niederprum et al. | |
| 4,990,643 A | 2/1991 | Traver | |
| 5,504,233 A | 4/1996 | Bindl et al. | |
| 5,637,746 A | 6/1997 | Knebelkamp et al. | |
| 6,127,573 A * | 10/2000 | Li et al. .................. | 562/419 |
| 6,169,213 B1 | 1/2001 | Fritz-Langhals et al. | |
| 6,750,371 B2 * | 6/2004 | Fritz-Langhals et al. ..... | 568/471 |
| 2003/0073871 A1 | 4/2003 | Fritz-Langhals et al. | |

FOREIGN PATENT DOCUMENTS

| | | |
|---|---|---|
| EP | 0 196 169 B1 | 3/1993 |
| EP | 0 569 189 A1 | 11/1993 |
| EP | 1 302 456 A1 | 4/2003 |
| WO | WO 99/52849 A | 10/1999 |

OTHER PUBLICATIONS

English Abstract corresponding to EP 1 302 456 A1.
Anelli, et al.: "Fast and Selective Oxidation of Primary Alcohols to Aldehydes or Tocarboxylic Acids and of Secondary Alcohols to Ketones Mediated by Oxoammonium Salts under Two-Phase Conditions", Journal of Organic Chemistry, American Chemical Society. Easton, US, vol. 52, No. 12, Jun. 12, 1987, pp. 2559-2562.
Enzyme Nomenclature, Academic Press, Inc., 1992, pp. 24-154.

* cited by examiner

*Primary Examiner* — Daniel M Sullivan
*Assistant Examiner* — Chukwuma O Nwaonicha
(74) *Attorney, Agent, or Firm* — Brooks Kushman P.C.

(57) ABSTRACT

Organosilicon compounds bearing carboxylic acid groups are easily and economically replaced in high yield by oxidation of a carbinol-functional organosilicon compound with an oxidizer in the presence of a moderator at a pH≧3. Carboxyl-functional organopolysiloxanes highly useful as textile softeners may be obtained by this method.

17 Claims, No Drawings

METHOD FOR THE PRODUCTION OF ORGANOSILICON COMPOUNDS COMPRISING CARBOXY RADICALS

CROSS-REFERENCE TO RELATED APPLICATION

This application is the U.S. national phase of PCT Appln. No. PCT/EP2005/051588 filed Apr. 11, 2005, which claims priority to German application 10 2004 019 376.2 filed Apr. 21, 2004.

BACKGROUND OF THE INVENTION

1. Field of the Invention

The invention relates to a method for the production of organosilicon compounds comprising carboxy radicals. 2. Description of the Related Art Organosilicon compounds comprising carboxy groups are used widely as textile finishing agents. For fabrics treated in this way, good soft-hand effects are achieved, coupled with a low yellowing tendency. In addition, organopolysiloxanes comprising carboxy groups are used in the finishing of leather and as release agents.

Various methods are known for producing carboxy-functional silanes or siloxanes. The insertion of the carboxylic acid groups via Grignard methods

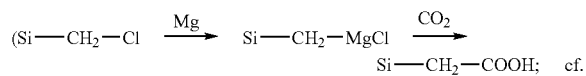

U.S. Pat. No. 2,763,675), from carboxyl compounds with activated CH group (reaction of haloalkylsiloxanes with cyanoacetic alkyl esters or malonic esters and subsequent hydrolysis including decarboxylation; cf. U.S. Pat. No. 3,391, 177), and the (co)hydrolysis of propionyl chloride-functional silanes (obtainable by chlorinating hydrosilylation of α,β-unsaturated carboxylic esters with halosilanes; cf. U.S. Pat. No. 3,143,524) are, however, less suited as industrial methods merely on the grounds of cost. Furthermore, the proposed processes place high requirements on the purity of the starting materials and the apparatus side of process control.

According to U.S. Pat. Nos. 2,900,363, 2,957,899 and 2,875,177, organosilicon compounds comprising carboxy groups can be obtained by hydrosilylation of acrylonitrile and subsequent, acid- or base-catalyzed hydrolysis. Disadvantages of these methods are the use of the toxicologically unacceptable acrylonitrile, the price of other suitable, unsaturated, nitrile-functional starting materials, and the hydrolysis being very slow on account of the heterogeneous reaction system, as a result of which a quantitative yield of free carboxylic acid groups can only be realized at very high cost.

Furthermore, organopolysiloxanes comprising carboxy groups are obtained by reacting SiH-functional compounds with unsaturated carboxylic acids in the presence of known hydrosilylation catalysts. The selectivity of the reaction, however, is very low since a significant secondary reaction which takes place is the condensation of SiH with the acidic proton of the acid group, which proceeds with the elimination of hydrogen, meaning that hydrolysis-labile, Si—O—C-linked structures are formed to a considerable degree.

It has therefore been proposed to replace the active hydrogen of the unsaturated carboxylic acid either with alkyl radicals (EP 569189 A) or a silyl radical (EP 196169 B1; U.S. Pat. No. 4,990,643) in order, following the addition reaction of said derivatives onto SiH-containing organosilicon compounds, to hydrolytically release the carboxylic acid group again. However, the methods are likewise very expensive since the hydrolysis of the silyl protective group and in particular of the alkyl esters requires, on account of the heterogeneous system, large amounts of water, long reaction times, high temperatures and—in the case of the alkyl esters—additionally strong acids and bases as catalyst, which in turn can lead to undesired secondary reactions on the siloxane backbone. Moreover, the water used in excess has to be removed again from the heterogeneous system when the reaction is complete, which is only possible through distillation with the help of an entrainer such as toluene since otherwise the mixture foams to a considerably high degree.

According to more recent patent specifications, silanes and siloxanes comprising carboxy groups can be obtained by adding a tertiary butyl ester with olefinic double bond, such as, for example, t-butyl methacrylate or t butyl undecenoate, onto an SiH-containing organosilicon compound in the presence of a hydrosilylation catalyst, and then converting the tertiary butyl ester group into the corresponding carboxylic acid group with thermal or catalytic cleavage of gaseous isobutene (U.S. Pat. Nos. 5,504,233, 5,637,746). The greatest disadvantage of this method is that the cleavage reaction proceeds smoothly only at elevated temperature, and in the process large volumes of a highly flammable, combustible gas with an extremely low flash point are generated. In particular, the explosive gas mixtures formed with air represent a considerable danger potential. The process can thus only be realized at high cost and requires special apparatus precautions and know-how. In addition, during the catalytic cleavage of the tert-butyl ester, strong acids, such as p-toluenesulfonic acid, methanesulfonic acid or trifluoromethanesulfonic acid, are used in amounts which can adversely affect the reaction, since these acids are also typical equilibration catalysts.

SUMMARY OF THE INVENTION

An object of the invention is thus to provide a cost-effective, simple and selective method for the production of organosilicon compounds comprising carboxy radicals; which makes the desired carboxy compounds accessible in a simple and rapid manner with high yields; and which satisfies the ever increasing requirements in the art with regard to space-time yield and universal applicability. These and other objects are achieved by the present invention wherein organosilicon compounds (2) comprising carboxy radicals are produced by oxidation of an organosilicon compound (1) comprising carbinol radicals with the help of a mediator (3) chosen from the group of aliphatic, cycloaliphatic, heterocyclic and aromatic

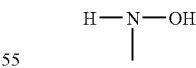

NO—, NOH— and -containing compounds and an oxidizing agent (4), with the proviso that the reaction is carried out with constant control of the pH at a pH of $\geq 3$, and that the carbinol radicals in the organosilicon compounds (1) used are oxidized predominantly to carboxy radicals.

DETAILED DESCRIPTION OF THE PREFERRED EMBODIMENTS

By the method according to the invention, advantageously at least 75 mol %, preferably at least 80 mol %, more preferably at least 85 mol %, and in particular at least 90 mol % of the carbinol radicals present in the organosilicon compounds (1) used are oxidized to carboxy radicals.

For the oxidation, all organosilicon compounds (1) are in principle suitable if they have primary carbinol groups.

Preferably, the organosilicon compounds (1) comprising carbinol radicals used in the method according to the invention are compounds comprising units of the formula $$A'_a R_b X_c H_d SiO_{(4-a-b-c-d)/2} \qquad (I),$$

where A' may be identical or different and is a radical of the formula $$-Y^1 \left( \begin{matrix} OH \\ H \\ H \end{matrix} \right)_{y-1}, \qquad (II)$$

$Y^1$ is a di- or polyvalent, linear or cyclic, branched or unbranched organic radical which may be optionally substituted and/or interrupted by the atoms N, O, P, B, Si and S, y corresponds to the valency of radical $Y^1$ and is $\geq 2$, R may be identical or different and is a monovalent, SiC-bonded optionally substituted hydrocarbon radical, X may be identical or different and is chlorine atom, the group A' or a radical of the formula $-OR^1$, where $R^1$ is a hydrogen atom or monovalent optionally substituted hydrocarbon radical which may be interrupted by heteroatoms, a is 0, 1 or 2, preferably 0 or 1, b is 0, 1, 2 or 3, c is 0, 1, 2 or 3, and d is 0, 1, 2 or 3, preferably 0, with the proviso that the sum a+b+c+d is $\leq 4$ and the organosilicon compound of the formula (I) has at least one radical A' per molecule.

The organosilicon compounds (2) comprising carboxy radicals obtained by the method according to the invention are compounds comprising units of the formula $$A_a R_b X_c H_d SiO_{(4-a-b-c-d)/2} \qquad (III),$$

where A may be identical or different and is a radical of the formula $$-Y^1 \left( \begin{matrix} O \\ OY^2 \end{matrix} \right)_{y-1}, \qquad (IV)$$

$Y^2$ is a hydrogen atom, an organic or inorganic cation, or a monovalent optionally substituted hydrocarbon radical which may be substituted by or interrupted by heteroatoms, in particular, N, O, P, B, Si, or S or groups containing these heteroatoms and $Y^1$, R, X, a, b, c, d and y have the meanings given for them above, with the proviso that the sum a+b+c+d is $\leq 4$ and the organosilicon compound of the formula (III) has at least one radical A per molecule.

The organosilicon compounds (1) used in the inventive method may either be silanes, i.e. compounds of the formula (I) where a+b+c+d=4, or polysiloxanes or organosilicone resins, i.e. compounds comprising units of the formula (I), where a+b+c+d$\leq$3, where, for the purposes of the present invention, the term polysiloxane should be understood to include polymeric, oligomeric and also dimeric siloxanes. The compounds (1) are preferably organopolysiloxanes and organosilicone resins, more preferably organopolysiloxanes, in particular those which consist only of units of the formula (I).

Preferably used as organosilicon compounds (1) comprising carbinol radicals are those of the formula $$A'_v R_w X_{(3-v-w)} Si \qquad (I')$$

$$A'_v R_{3-v} SiO(SiR_2O)_n(SiRA'O)_o SiR_{3-v} A'_v \qquad (I''), \text{ and}$$

$$[A'_v R_{3-v} SiO_{1/2}]_s [SiO_{4/2}] \qquad (I'''),$$

where A', R and X have the meanings given for them above, v is 0, 1, 2 or 3, preferably 0 or 1, w is 0, 1, 2 or 3, n is 0 or an integer from 1 to 2000, o is 0 or an integer from 1 to 2000, preferably 0 to 500, s can assume a value of from 0.2 to 6, preferably 0.4 to 4, inclusive and describes the number of M units $[A'_v R_{3-v} SiO_{1/2}]$ per Q unit $[SiO_{4/2}]$ in the organosilicone resin, with the proviso that they comprise at least one radical A' per molecule.

Preferred organosilicon compounds (2) comprising carboxy radicals are therefore those of the formula $$A_v R_w X_{(3-v-w)} Si \qquad (III'),$$

$$A_v R_{3-v} SiO(SiR_2O)_n(SiRAO)_o SiR_{3-v} A_v \qquad (III''), \text{ and}$$

$$[A_v R_{3-v} SiO_{1/2}]_s [SiO_{4/2}] \qquad (III'''),$$

where A, R, X, v, w, n, o and s have the meanings given for them above, with the proviso that they comprise at least one radical A per molecule.

Examples of radical R are alkyl radicals such as the methyl, ethyl, n-propyl, isopropyl, 1-n-butyl, 2-n-butyl, isobutyl, tert-butyl, n-pentyl, isopentyl, neopentyl, and tert -pentyl radicals; hexyl radicals such as the n-hexyl radical; heptyl radicals such as the n heptyl radical; octyl radicals such as the n-octyl radical and isooctyl radicals such as the 2,2,4-trimethylpentyl radical; nonyl radicals such as then nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl, and methylcyclohexyl radicals; alkenyl radicals such as the vinyl, 1 propenyl and 2-propenyl radicals; aryl radicals, such as the phenyl, naphthyl, anthryl and phenanthryl radicals; alkaryl radicals such as the o-, m-, and p-tolyl; radicals, xylyl radicals and ethylphenyl radicals; and aralkyl radicals such as the benzyl radical, and the α- and the β-phenylethyl radicals.

Examples of substituted radicals R are haloalkyl radicals such as the 3,3,3-trifluoro-n-propyl radical, the 2,2,2,2',2',2'-hexafluoroisopropyl radical, and the heptafluoroisopropyl radical; haloaryl radicals such as the o-, m- and p-chlorophenyl radicals; acylated aminoalkyl radicals such as the N-acetylaminopropyl, N acetylcyclohexylaminopropyl, N-acetyldimethylaminopropyl, N-acetyldiethylaminopropyl and N,N'-diacetylaminoethylaminopropyl Radicals; quat-functional radicals such as $-(CH_2)_3-N(CH_3)_3^+$ and $-(CH_2)_3-NH-CH_2-CH(OH)-CH_2-N(CH_3)_3^+$, including the anions required to compensate for the cationic charge; hydroxyl-functional radicals such as those from sec. or tert. aliphatic or aromatic alcohols, for example, the phenol and eugenol radicals; carboxylic-acid-functional radicals, and derivatives or salts thereof, such as the acetic acid, 3-carboxypropyl, 4 carboxybutyl, 10-carboxydecyl, 3-(2,5-dioxotetrahydrofuranyl)propyl, 3-(ethane-1,2-dicarboxylic acid) propyl, 3-acryloxypropyl, 3-methacryloxypropyl or undecenesilyl ester radicals; epoxy-functional radicals, for example,

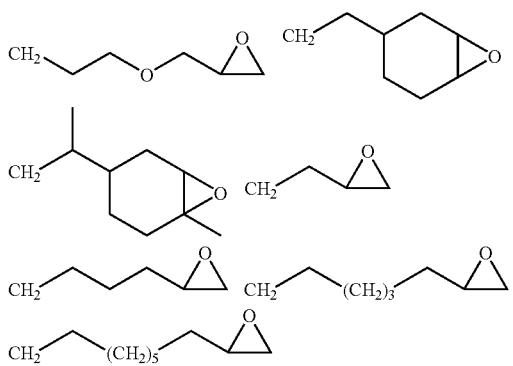

ketone-functional radicals; alkyl- or acyl-terminated, SiC- or SiOC-bonded polyalkylene oxide radicals such as those which are derived from polyethylene glycol, polypropylene glycol, poly(1,4-butanediol) and mixed polymers thereof; phosphonato-functional radicals, for example, phosphonatoalkyl radicals; silalactone-functional radicals; and glycoside-functional radicals, such as those in which the glycoside radical, which may contain from 1 to 10 monosaccharide units, is bonded via an alkylene or oxyalkylene spacer, and in which at least some primary hydroxy groups are provided with acyl or alkyl protective groups.

The radical R is preferably a hydrocarbon radical having 1 to 18 carbon atom(s) optionally substituted by halogen groups, tert-hydroxy groups, acylated amino groups, groups comprising quaternary nitrogen, carboxylic acid or carboxylic acid derivative groups or epoxy groups, or is an alkyl- or acyl-terminated SiC- or SiOC-bonded polyalkylene oxide radical, more preferably the methyl, ethyl, vinyl, n-propyl, n-octyl, n-dodecyl, n-octadecyl and phenyl radical, and in particular a methyl or phenyl radical. If the organosilicon compounds are organopolysiloxanes, at least 50%, more preferably at least 90% of all radicals R are methyl or phenyl radicals.

Examples of radicals $R^1$ are the examples given for radical R. Preferably, the radical $R^1$ is a hydrogen atom or an alkyl radical having 1 to 8 carbon atom(s), optionally interrupted by ether oxygen atoms. Particular preference is given to the hydrogen atom, and the methyl, ethyl, propyl and butyl radicals.

Examples of radical X are the chlorine atom, the OH group, the group A', and alkoxy radicals such as the methoxy, ethoxy, n-propoxy, isopropoxy, 1-butoxy, 2-butoxy, 1 pentyloxy, 1-hexyloxy, 1-octyloxy, 2-octyloxy, isooctyloxy, 1-decyloxy, 1-dodecyloxy, myristyloxy, cetyloxy and stearyloxy radicals. Radical X is preferably a chlorine atom, the radical A', the OH group, or the methoxy, ethoxy, propoxy, butoxy, myristyloxy, cetyloxy or stearyloxy radical, most preferably a chlorine atom, the OH group, or a methoxy, ethoxy, propoxy or butoxy radical.

Examples of radical $Y^1$ are alkylene radicals such as the methylene, ethylene, propylene, 2-methylpropylene, butylene, pentylene, hexylene, heptylene, octylene, nonylene, undecylene and heptadecylene radicals; cyclic and polycyclic alkylene radicals such as the cyclohexylene, methylcyclohexylene, dimethylcyclohexylene and norbornylene radicals; unsaturated alkylene radicals such as the ethenylene, 1-propenylene, 1 butenylene and 2-butenylene radicals; ether- and polyether-functional alkylene radicals; and alkylene radicals which are interrupted by a carboxylic acid derivative group, for example a carboxylic ester or carboxamide group, or a carbonic acid derivative group such as a carbonic ester, urethane or urea group.

Radical $Y^1$ is preferably a di- to decavalent, preferably di- to pentavalent, hydrocarbon radical optionally substituted by one or more units —C(O)—, —C(O)O—, —C(O)NR$^1$—, —O—C(O)O—, —O—C(O)NR$^1$—, —NR$^1$—C(O)—NR$^1$—, —O—, —S— and substituted by tert-hydroxy, alkoxy, mercaptoalkyl, carbonyl, carboxyl, nitrile or oxiranyl groups.

Preferably, radical $Y^1$ is
A) the ethylene, propylene, 2-methylpropylene, butylene, pentylene, nonylene and undecylene radical, the radicals

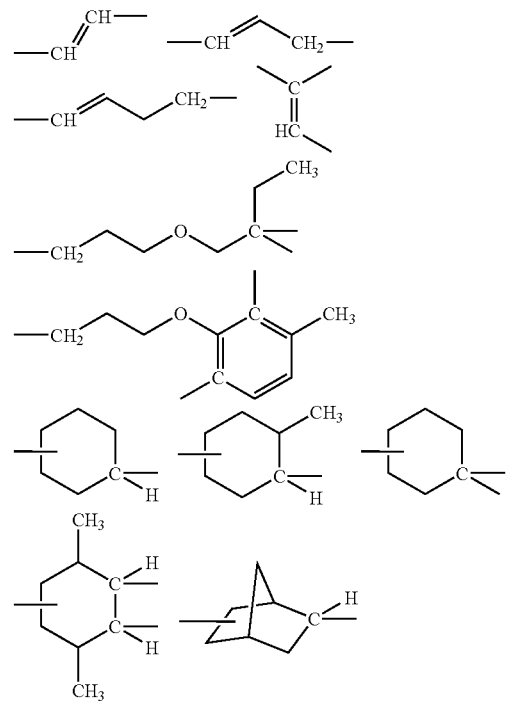

B) a radical of the formula

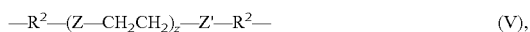

where the radicals $R^2$ may be identical or different and are a divalent hydrocarbon radical having 1 to 10 (preferably 1 to 6) carbon atoms, Z is the unit —O— or —N[—C(O)—(CH$_2$)$_h$—H]—, where h≧1 (preferably 1-6, particularly preferably 1-3), and Z' is the groups —O—C(O)—, —NH—C(O)—, —O—C(O)O—, —NH—C(O)O— or —NH—C(O)NH—, preferably —O—C(O)— or —NH—C(O)—, and z is an integer from 0 to 4 (preferably 0 or 1), or
C) a radical of the formula

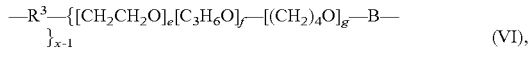

where $R^3$ is a divalent, trivalent or tetravalent organic radical having 2 to 10 carbon atoms which may be substituted by one or more units

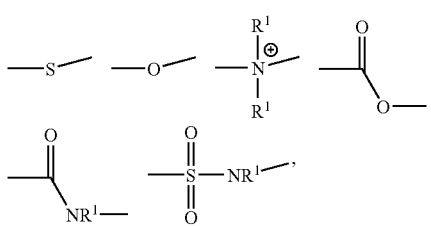

B is a methylene, ethylene or n-propylene spacer, e, f, g, independently of one another, are each 0 or an integer from 1-200, preferably 0-100, particularly preferably 0-50, with the proviso that the sum e+f+g is $\geq 1$, and x corresponds to the valency of radical $R^3$ and can assume the value 2, 3 or 4.

Radical $Y^1$ is particularly preferably the ethylene, propylene, 2-methylpropylene, butylene, pentylene, nonylene and undecylene radical, the radicals

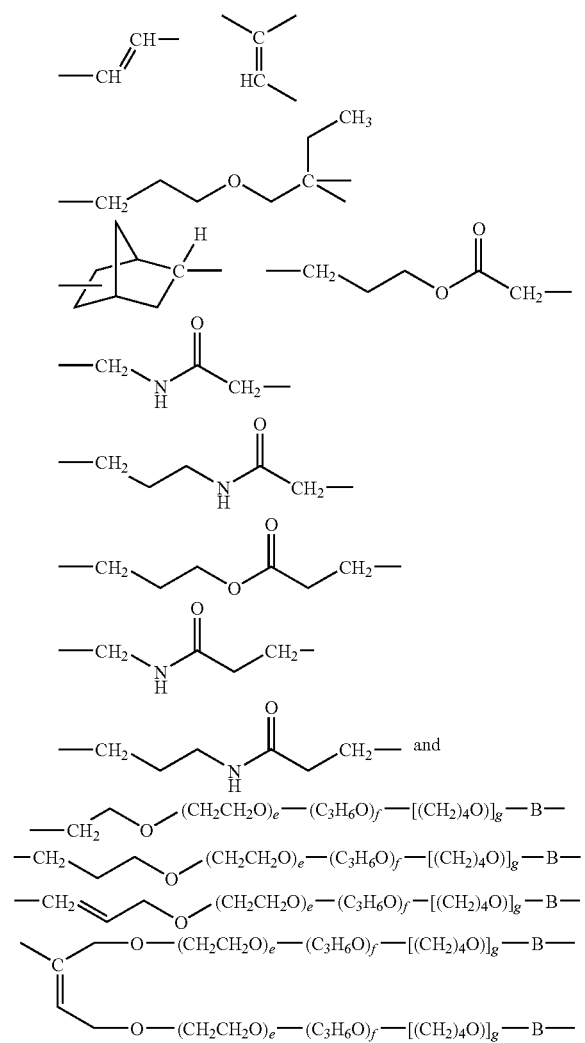

with B, e, f and g in the meanings given for them above.

Preferably y corresponds to the valency of $Y^1$ and is an integer from 2 to 10, preferably 2 to 5.

Preferably, radical $Y^2$ is hydrogen atom, an organic or inorganic cation or a monovalent hydrocarbin radical having 1 to 18 carbon atom(s), more preferably hydrogen atom, tetraalkylammonium, trialkylanunonium, dialkylammonium, alkylanunonium, ammonium, lithium, sodium, potassium and cesium.

The mediator (3) used is preferably at least one compound chosen from the group of aliphatic, cycloaliphatic, heterocyclic or aromatic compounds which comprises at least one N-hydroxy, oxime, nitroso, N-oxyl or N-oxy function. Examples of such compounds are described in detail in U.S. Pat. No. 6,169,213 B1 (incorporated by reference), in particular column 5, line 63 to column 25, line 58, and US 2003073871 A1 (incorporated by reference), in particular page 2, paragraph [0023] to page 3, paragraph [0030] inclusive.

Preferred mediators (3) are nitroxyl radicals of the general formulae (XI) and (XII)

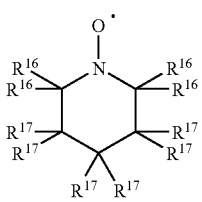

(XI)

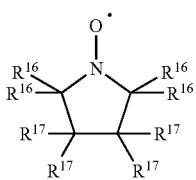

(XII)

where $R^{16}$ is identical or different and is phenyl, aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical, where the phenyl radicals may be unsubstituted or mono- or polysubstituted by a radical $R^{18}$, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals may be saturated or unsaturated, branched or unbranched and may be mono- or polysubstituted by a radical $R^{18}$, where $R^{18}$ may be present one or more times and is identical or different and is hydroxy, formyl, carboxy radical, ester or salt of the carboxy radical, carbamoyl, sulfono, sulfamoyl, nitro, nitroso, amino, phenyl, benzoyl, $C_1$-$C_5$-alkyl, $C_1$-$C_5$-alkoxy radical, $C_1$-$C_5$-alkylcarbonyl, $R^{17}$ is identical or different and is a hydrogen atom or hydroxy, mercapto, formyl, cyano, carbamoyl, carboxy radical, ester or salt of the carboxy radical, sulfono radical, ester or salt of the sulfono radical, sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical, phospho, phosphono, phosphonooxy radical, ester or salt of the phosphonooxy radical, where the carbamoyl, sulfamoyl, amino, mercapto and phenyl radicals may be unsubstituted or mono- or polysubstituted by a radical $R^{12}$, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals may be saturated or unsaturated, branched or unbranched and may be mono- or polysubstituted by a radical $R^{12}$, and a [—$CR^{17}R^{17}$—] group may be replaced by oxygen, an optionally $C_1$-$C_5$-alkyl-substituted imino radical, a (hydroxy)imino radical, a carbonyl function or a vinylidene function optionally mono- or disubstituted by $R^{12}$, and two adjacent groups [—$CR^{17}R^{17}$—] may be replaced by a group [—$CR^{17}$=$CR^{17}$—], [—$CR^{17}$=N—] or [—$CR^{17}$=N(O)—].

Mediators (3) preferably used according to the method of the invention are:
2,2,6,6-tetramethylpiperidin-1-oxyl (TEMPO),
4-hydroxy-2,2,6,6-tetramethylpiperidin-1-oxyl,
4-acetamido-2,2,6,6-tetramethylpiperidin-1-oxyl,
4-acetoxy-2,2,6,6-tetramethylpiperidin-1-oxyl,
4-benzoyloxy-2,2,6,6-tetramethylpiperidin-1-oxyl,
PIPO (polymer immobilized piperidinyloxyl),
3-amino-N-hydroxyphthalimide,
4-amino-N-hydroxyphthalimide,
N-hydroxyphthalimide,
3-hydroxy-N-hydroxyphthalimide,
3-methoxy-N-hydroxyphthalimide,
3,4-dimethoxy-N-hydroxyphthalimide,
4,5-dimethoxy-N-hydroxyphthalimide,
3,6-dihydroxy-N-hydroxyphthalimide,
3,6-dimethoxy-N-hydroxyphthalimide,
3-methyl-N-hydroxyphthalimide,
4-methyl-N-hydroxyphthalimide,
3,4-dimethyl-N-hydroxyphthalimide,
3,5-dimethyl-N-hydroxyphthalimide,
3,6-dimethyl-N-hydroxyphthalimide,
3-isopropyl-6-methyl-N-hydroxyphthalimide,
3-nitro-N-hydroxyphthalimide,
4-nitro-N-hydroxyphthalimide,
1-hydroxy-1H-benzotriazole,
violuric acid,
N-hydroxyacetanilide,
3-nitrosoquinoline-2,4-diol,
2,4-dihydroxy-3-nitrosopyridine,
2,6-dihydroxy-3-nitrosopyridine,
2,4-dinitroso-1,3-dihydroxybenzene,
2-nitroso-1-naphthol-4-sulfonic acid and
1-nitroso-2-naphthol-3,6-disulfonic acid,
where
2,2,6,6-tetramethylpiperidin-1-oxyl (TEMPO),
4-hydroxy-2,2,6,6-tetramethylpiperidin-1-oxyl,
4-amino-2,2,6,6-tetramethylpiperidin-1-oxyl,
4-acetoxy-2,2,6,6-tetramethylpiperidin-1-oxyl,
4-benzoyloxy-2,2,6,6-tetramethylpiperidin-1-oxyl and
PIPO (polymer immobilized piperidinyloxyl)
are particularly preferred.

In one particular embodiment, the nitroxyl radicals of the general formulae (XI) and (XII) can also be linked to a polymeric structure via one or more radicals $R^{17}$. The literature describes a large number of such polymer-bound nitroxyl radicals (cf. e.g. the literature cited in EP 1 302 456 A1, page 4, lines 39 to 43). Examples are PIPO (polymer immobilized piperidinyloxyl), $SiO_2$-supported TEMPO, polystyrene- and polyacrylic-acid-supported TEMPO.

According to the method of the invention, the mediator (3) is preferably used in amounts of from 0.01 to 100 mol %, more preferably 0.1 to 20 mol %, and most preferably 0.1 to 5 mol %, based on the molar amount of carbinol groups present in the organosilicon compounds used.

The method of the invention can be carried out with one or more of the described mediators (3), preferably with one or two mediators (3), most preferably with one mediator (3). The mediator (3) can be dissolved in an organic or aqueous phase or may be used in supported form as an independent phase.

According to the invention, the corresponding, active oxoammonium species is produced from the mediator (3) in situ by the oxidizing agent and is not isolated. In one particular embodiment, however, the mediator (3) can be converted into the active oxoammonium species in a separate upstream oxidation reaction, isolated and then used separately.

In the inventive method, the oxidizing agents (4) used are preferably air, oxygen, hydrogen peroxide, organic peroxides, perborates or persulfates, organic or inorganic peracids, salts and derivatives of the peracids, chlorine, bromine, iodine, hypohalic acids and salts thereof, e.g. in the form of bleaching liquor, halic acids and salts thereof, halogen acids and salts thereof, $Fe(CN)_6^{3-}$, and N-chloro compounds. Oxidizing agents may, for example, however, also be metal oxides or anodes of electrolysis cells. Furthermore, the oxidizing agent used can also be generated in situ, e.g. electrochemically; by hydrolysis, for example, by hydrolysis of N chloro compounds; or by redox reactions, for example, in the case of hypochlorite or hypobromite solutions, by disproportionation of chlorine or bromine, respectively, in alkaline solution, or, for example, the redox reaction between hypochlorite and bromide which leads to the formation of hypobromite.

In the case of salt-like oxidizing agents, sodium, potassium, calcium, ammonium or tetraalkylammonium are preferred as counterions.

The oxidizing agents (4) can be used individually or in a mixture, if appropriate in each case in combination with enzymes, where, for the purposes of the invention, the term enzyme also includes enzymatically active proteins or peptides or prosthetic groups of enzymes.

Examples of enzymes which can be used for the purposes of the method according to the invention are described in detail in U.S. Pat. No. 6,169,213 B1 (column 26, line 29 to column 28, line 6), where oxidoreductases of classes 1.1.1 to 1.97 according to the International Enzyme Nomenclature, Committee of the International Union of Biochemistry and Molecular Biology (Enzyme Nomenclature Academic Press, Inc., 1992, p. 24-154) are preferably used.

If enzymes are used, preference is given to using oxidoreductases of the classes specified below:
enzymes of class 1.1.5 (quinones as acceptor),
enzymes of class 1.1.3 (oxygen as acceptor),
enzymes of class 1.2.3 (oxygen as acceptor),
enzymes of class 1.3.3 (oxygen as acceptor),
enzymes of class 1.3.5 (quinones as acceptor),
enzymes of class 1.4.3 (oxygen as acceptor),
enzymes of class 1.5.3 (oxygen as acceptor),
enzymes of class 1.5.5 (quinones as acceptor),
enzymes of class 1.6.5 (quinones as acceptor),
enzymes of class 1.7.3 (oxygen as acceptor),
enzymes of class 1.8.3 (oxygen as acceptor),
enzymes of class 1.8.5 (quinones as acceptor),
enzymes of class 1.9.3 (oxygen as acceptor),
enzymes of class 1.10.3 (oxygen as acceptor),
peroxidases of class 1.11.1,
and enzymes of classes 1.12, 1.13, 1.14, 1.15 and 1.16, where
cellobiose: quinone-1-oxidoreductase (1.1.5.1),
bilirubin oxidase (1.3.3.5),
catechol oxidase (tyrosinase) (1.10.3.1),
L-ascorbate oxidase (1.10.3.3),
o-aminophenol oxidase (1.10.3.4)
laccase (benzenediol: oxigen oxidoreductase) (1.10.3.2)
cytochrome-C-peroxidases (1.11.1.5),
catalase (1.11.1.6),
peroxidase (1.11.1.7),
iodide peroxidase (1.11.1.8),
glutathione peroxidase (1.11.1.9),
chloride peroxidase (1.11.1.10), L-ascorbate peroxidase (1.11.1.11),
phospholipid hydroperoxide glutathione peroxidase (1.11.1.12),
manganese peroxidase (1.11.1.13),
diarylpropane peroxidase (ligninase, lignin peroxidase) (1.11.1.14),
superoxide dismutase (1.15.1.1) and
ferroxidase (1.16.3.1)
are particularly preferred.

The specified enzymes are commercially available or can be obtained by standard methods. Suitable organisms for producing the enzymes are, for example, plants, animal cells, bacteria and fungi. In principle, naturally occurring and also genetically modified organisms may be enzyme producers. Parts of single-cell or multicell organisms are likewise conceivable as enzyme producers, primarily cell cultures. For the particularly preferred enzymes, such as those from the group 1.11.1, but primarily 1.10.3, and in particular for the production of laccases, white rot fungi such as *Pleurotus, Phlebia* and *Trametes*, are used.

The oxidizing agents (4) used are preferably used in concentrations of 0.1 M up to their respective saturation concentration.

If the oxidizing agent (4) is a 2-electron oxidizing agent, then this agent is preferably used in an amount of from 0.2 to 250 mol %, more preferably 100 to 220 mol %, and most preferably 150 to 210 mol %, in each case based on the molar amount of the carbinol groups present in the organosilicon compounds. If, by contrast, the oxidizing agent is a 1-electron oxidizing agent, then this agent is preferably used in an amount of from 0.4 up to 500 mol %, preferably 200 to 440 mol %, and most preferably 300 to 420 mol %, in each case based on the molar amount of the carbinol groups present in the organosilicon compounds.

If, in the method according to the invention, metal oxides are used as oxidizing agents (4), bismuth(III) oxide, iridium (III) oxide, cerium(IV) oxide, cobalt(II) oxide, cobalt(III) oxide, iron(III) oxide, manganese(IV) oxide, tin(IV) oxide, niobium(V) oxide, antimony(V) oxide, indium(III) oxide, mercury(II) oxide, lead(IV) oxide, silver(I) oxide, Cu(II) oxide, palladium(II) oxide, in particular lead(IV) oxide, manganese(IV) oxide, silver(I) oxide, Cu(II) oxide and palladium (II) oxide are preferred.

If, in the method according to the invention, the oxidation takes place with the help of electrodes of an electrolysis cell, then the electrodes used may be identical or different and preferably consist of carbon, iron, lead, lead dioxide, copper, nickel, zinc, cadmium, mercury, tantalum, titanium, silver, platinum, platinized platinum, palladium, rhodium, gold or of alloys of said compounds. Particular preference is given to electrodes made of stainless steel, tantalum, titanium, rhodium, platinum or gold, in particular electrodes made of stainless steel, with stainless steels of group 1.4xxx (according to DIN 17850) being very particularly preferred.

The electrodes may optionally have been coated with other substances by deposition, sputtering, galvanization or similar methods. The surface area of the electrodes may have been increased by suitable methods, for example by grinding, polishing, sandblasting, etching or erosion.

In addition, in the method according to the invention, all further substances (5) which have also hitherto been used in mediated oxidations can be used. Possible additives are halogens, e.g. bromine, or salts, e.g. alkali metal, alkaline earth metal or ammonium halides or sulfates, carbonates, hydrogen carbonates, phosphoric acid and alkali metal, alkaline earth metal or ammonium salts thereof or carbon dioxide. These additives can be added to the oxidizing agent or to the phase comprising the oxidizing agent or to the organosilicon compound (1) to be oxidized or to the phase comprising the organosilicon compound (1) to be oxidized, optionally in dissolved form, or can be fed to the reaction mixture optionally in dissolved form as further component.

If, in the method according to the invention, hypochlorite, for example, is used as oxidizing agent (4), the addition of bromine or bromide, which is preferably used in amounts of from 0.01 to 100 mol %, based on the amount of hypochlorite used, preferably in amounts of between 1 and 50 mol %, for example, is preferred.

In addition, in the method according to the invention, substances (6) are added to the reaction mixture with whose help the pH of the reaction mixture can be changed or kept constant. Examples of such substances (6) are buffers such as sodium hydrogen carbonate, disodium hydrogen phosphate or sodium dihydrogen phosphate, or buffer mixtures; acids such as carbon dioxide, phosphoric acid, hydrochloric acid or sulfuric acid; and bases such as alkali(ne earth) metal hydroxides, carbonates or phosphates, such as NaOH, KOH, $Na_2CO_3$ or $Na_3PO$ The method according to the invention can be carried out with or without additional solvents (7) as 1-phase or multiphase reaction or in dispersion, such as, for example, microemulsion or macroemulsion.

If, in the method according to the invention, solvent (7) is used, it is preferably an inert solvent which does not influence the redox process. Examples of suitable solvents (7) which can be used individually or in a mixture with one another, are pentane, petroleum ether, n-hexane, hexane isomer mixtures, cyclohexane, heptane, octane, solvent naphtha, decalin, benzene, toluene, xylene, diethyl ether, di-n-propyl ether, diisopropyl ether, di-n-butyl ether, methyl tert-butyl ether, ethylene glycol dimethyl ether, ethylene glycol diethyl ether, diethylene glycol dimethyl ether, tetrahydrofuran, dioxane, methyl acetate, ethyl acetate, n-, sec- and tert-butyl acetate, dichloromethane, trichloromethane, tetrachloromethane, 1,2-dichloroethane, trichloroethylene, tetrachloroethylene, chlorobenzene, 1-chloronaphthalene, ethylene carbonate, propylene carbonate, $CO_2$, acetonitrile, acetamide, tetrahydro-1,3-dimethyl-2(1H)-pyrimidinone (DMPU), hexamethylphosphortriamide (HMPT), dimethyl sulfoxide (DMSO), sulfolane, acetone, methyl ethyl ketone (MEK), methyl isobutyl ketone (MIBK), diisopropyl ketone, ionic liquids, linear and cyclic siloxanes, and mixtures of said solvents.

If additional solvents (7) are used, the amounts are preferably from 0.1 to 200 parts by weight, more preferably 1 to 100 parts by weight, in each case based on 100 parts by weight of the weight of the organosilicon compound (1) to be oxidized.

If the method according to the invention is carried out as 2-phase reaction, then the homogenization of the immiscible phases and the provision of a large internal reaction area is desired to be very effective, for example, by generating an average particle size of <500 µm. The intense thorough mixing of the reaction phases can take place in principle with all mixing systems known according to the prior art, for example, conventional stirrers of all types, high-speed stirrers such as those available under the trade mark Ultra-Turrax® or similar dissolver systems, by means of ultrasound probes or baths, electric, magnetic or electromagnetic fields etc., or, for example, when carrying out the reaction continuously, with static or moving mixing elements or nozzles, and through turbulent flow, or through any combinations thereof.

If the method according to the invention is carried out in dispersion, then emulsifiers or surface-active agents (8) such as nonionic, anionic, cationic or amphoteric emulsifiers, may accordingly be present, where the dispersion can be produced in any manner known to the person skilled in the art. However, the emulsifier or surface-active agent which may be used may also be the organosilicon compound (1) to be oxidized, or the reaction product (2) obtained by the method according to the invention.

The components used in the method according to the invention may in each case be one type of such a component, or a mixture of at least two types of a particular component.

In the inventive method, the components used can be arbitrarily mixed together, fed to the reaction and/or reacted in a manner known per se. The method can be carried out batchwise, semicontinuously or entirely continuously in reactor systems suitable for this purpose, for example, batch reactors, batch reactor cascades, loop reactors, stream tubes, tubular reators, microreactors, centrifugal pumps, and any combinations thereof.

In the case of a strongly exothermic reaction and/or batchwise procedure, a metered addition of components (4), optionally in a mixture with component (6), to a mixture consisting of components (1), (3) and (6) and optionally (5), (7) and/or (8) is preferred. In the case of a continuous procedure, a cometering of three volume streams, consisting of volume stream A containing components (1) and (3) and optionally (7) and/or (8), volume stream B containing components (5) and (6) and volume stream C containing component (4) optionally in a mixture with component (6) preferably takes place.

The method is preferably carried out with constant monitoring of the pH at a pH of $pH \geqq 3$ and $pH \leqq 12$, more preferably $pH \geqq 4$, and most preferably $pH \geqq 6$. The pH is adjusted here preferably during the reaction through the simultaneous addition of component (6). If desired, component (6) can also be added in a sufficient amount before the reaction and the pH of the reaction mixture can therefore be kept constant for the duration of the reaction.

In addition, the method according to the invention is preferably carried out at a temperature of from −100 to +150° C., more preferably −50 to +100° C., and most preferably −20 to +75° C. The reaction times are preferably 0.1 seconds to 72 hours, more preferably 1 second to 48 hours, and most preferably 1 second to 24 hours.

When the reaction is complete, the reaction products can be separated off from any reaction auxiliaries used and isolated by any hitherto known process steps. Preferably, the products are isolated in the form of their free acids by acidifying the reaction mixture to pH values $\leqq 3$. The acids used here are preferably those whose pKa value is less than the pKa value of the carboxy group of the organosilicon compounds (2) comprising carboxy radicals according to the invention. Examples of such acids are trifluoroacetic acid, HCl, $H_2SO_4$, methanesulfonic acids, trifluoromethanesulfonic acids and p-toluenesulfonic acids. As a result, the formed free siloxanecarboxylic acids soluble in organic medium are also separated off from salts present, e.g. inorganic salts. If desired, after the reaction, readily volatile components and any solvent used can also be removed by distillation.

Furthermore, the method according to the invention can be followed by any further process steps, by means of which the desired properties of the organosilicon compound (2) obtained by the method according to the invention can be adjusted in a targeted manner. The procedure of the process steps is governed here primarily by the current prior art and takes place in the manner known to the person skilled in the art.

Examples of such consecutive reactions are, in particular, equilibration reactions with, for example, organopolysiloxanes, condensation of the organosilicon compound (2) with other organosilicon compounds capable of condensation reactions, for example, silanols, alkoxy-functional silanes and silanol- or alkoxy-functional polysiloxanes or organosilicone resins, and also the organofunctional modification of the organosilicon compound, for example, esterification, amide formation or anhydride formation.

The method according to the invention offers a number of advantages over the prior art. It is preparatively simple to realize without special expenditure on apparatus and, due to the low reaction temperature and the catalytic use of the mediators employed, cost-effective, resource-conserving and thus sustainably environmentally compatible.

The method according to the invention can be used universally and flexibly. It is equally suitable for a discontinuous and in particular a continuous procedure, which means a further advantage with regard to costs, flexibility and space-time yield.

Through the selective, rapid and virtually quantitative oxidation of the carbinol groups, excellent reaction yields are obtained in short reaction times even in the case of polymeric organosilicon compounds. The reaction products can be isolated cleanly and in a simple manner. In addition, scarcely any by-products are formed in the reaction according to the invention. Furthermore, the relatively mild reaction conditions permit the use of the method according to the invention also on organosilicon compounds (1) with sensitive functional groups.

The carboxy-radical-comprising organosilicon compounds (2) obtained by the method according to the invention are exceptionally suitable, for example, on account of the reactivity of the carboxy group toward O, N and S nucleophiles, for the permanent finishing of corresponding materials, such as, for example, of natural fibers (wool, silk, cotton, keratin fibers, etc.), cellulose and cellulose fibers, and blends thereof with synthetic fibers such as polypropylene, polyester or polyamide fibers. Typical target effects are a soft, flowing feel, low tendency toward yellowing, improved elasticity, antistatic properties, low coefficients of friction, surface smoothness, shine, crease recovery, colorfastnesses, washing resistance, hydrophilicity, tear-propagation resistance, reduced pilling tendency, "easy-care" and "soil-release" properties, improved wear comfort, high resistance of the finishing to washing and care processes, improved industrial processability, e.g. with regard to rate of processing and production.

In addition, the organosilicon compounds (2) comprising carboxy radicals are suitable as auxiliaries in the tanning and dressing of leather, and also for the sizing and surface refining of paper. Organosilicon compounds comprising carboxy radicals can also be used as additives in coatings and paints, where they lead, for example, to a reduction in the surface roughness and thus to a reduction in the slip resistance of the paint.

Other use possibilities are the use as additive in cosmetic formulations, for example in skincare compositions, as conditioner in hair-washing compositions or as humectants generally.

In addition, silicones comprising carboxy radicals are used in protective compositions for buildings, and, as surface-active substances, for producing aqueous emulsions.

Moreover, organosilicon compounds comprising carboxy radicals can also be used as a chemical building block, for example, for producing plastics or resins, and as an intermediate for further syntheses.

The process examples below explain the invention. Unless stated otherwise, all indications of parts with percentages are based on the weight. Furthermore, all viscosity data refer to a temperature of 25° C. Unless stated otherwise, the examples below are carried out at the pressure of the ambient atmosphere, i.e. at about 1000 hPa, and at room temperature, i.e. at about 20° C., or at a temperature which is established upon combining the reactants at room temperature without additional heating or cooling.

EXAMPLE 1

3-[2-(2-Carboxyethyl)-1,1,2,2-tetramethyl-disiloxanyl]propionic acid 20 g (80 mmol) of 3-[2-(3-hydroxypropyl)-1,1,2,2-tetramethyldisiloxanyl]propanol are dissolved together with 758 mg (4.4 mmol) of 4-hydroxy-TEMPO in 40 ml of ethyl acetate. 166 ml of technical bleaching liquor are adjusted to a pH of 9.5 with 20 percent sulfuric acid. Synchronously, these solutions are added dropwise to a reaction vessel cooled to 0° C. with vigorous stirring. The pH of the reaction mixture is maintained at about 8 through the simultaneous addition of 2N NaOH.

The phases are separated, and the aqueous phase is washed with 10 ml of ethyl acetate and acidified with conc. HCl to pH 1. Extraction with MTBE and concentration by evaporation gives 19 g of solid, which is pure 3-[2-(2-carboxyethyl)-1,1,2,2-tetramethyl-disiloxanyl]propionic acid.

EXAMPLE 2

α,ω-(2-Carboxyethyl)-modified polydimethylsiloxane

The reaction takes place analogously to Example 1 using a polysiloxane consisting of dimethylsiloxy and (3-hydroxypropyl)dimethylsiloxy units with a carbinol group content of 3.19% by weight and a viscosity of about 50 mPa·s (at 25° C.). When the reaction is complete, the neutral reaction mixture is acidified with 10% strength HCl, the ethyl acetate phase is separated off and the mixture is concentrated by evaporation. This gives the α,ω-(2-carboxyethyl)-modified polydimethylsiloxane as a virtually colorless, clear oil with a carboxy group content of 8.23% by weight.

EXAMPLE 3

α,ω-(2-Carboxyethyl)-modified polydimethylsiloxane

The reaction takes place analogously to Example 1 using a polysiloxane consisting of dimethylsiloxy and (3-hydroxypropyl)dimethylsiloxy units with a carbinol group content of 0.81% by weight and a viscosity of about 110 mPa·s (at 25° C.). When the reaction is complete, the neutral reaction mixture is acidified with 10% strength HCl, the ethyl acetate phase is separated off and the mixture is concentrated by evaporation. This gives the α,ω-(2-carboxyethyl)-modified polydimethylsiloxane as a virtually colorless, clear oil with a carboxy group content of 2.14% by weight.

EXAMPLE 4 laterally 2-carboxyethyl-modified polydimethylsiloxane

The reaction takes place analogously to Example 1 using a polysiloxane consisting of trimethylsiloxy, dimethylsiloxy and (3-hydroxypropyl)methylsiloxy units with a carbinol group content of 4.4% by weight and a viscosity of about 350 mPa·s (at 25° C.). When the reaction is complete, the neutral reaction mixture is acidified with 10% strength HCl, the ethyl acetate phase is separated off and the mixture is concentrated by evaporation. This gives the α,ω-(2-carboxyethyl)-modified polydimethylsiloxane as a slightly yellowish, clear oil with a carboxy group content of 11.6% by weight.

EXAMPLE 5 laterally 2-carboxyethyl-modified polydimethylsiloxane

The reaction takes place analogously to Example 1 using a polysiloxane consisting of trimethylsiloxy, dimethylsiloxy and 3-(hydroxypropyl)methylsiloxy units with a carbinol group content of 1.08% by weight and a viscosity of about 550 mPa·s (at 25° C.). When the reaction is complete, the neutral reaction mixture is acidified with 10% strength HCl, the ethyl acetate phase is separated off, and the mixture is concentrated by evaporation. This gives the α,ω-(2-carboxyethyl)-modified polydimethylsiloxane as a pale yellow, clear oil with a carboxy group content of 2.85% by weight.

EXAMPLE 6 laterally 2-carboxyethyl-modified polydimethylsiloxane

The reaction takes place analogously to Example 1 using a polysiloxane consisting of trimethylsiloxy, dimethylsiloxy and (3-hydroxypropyl)methylsiloxy units with a carbinol group content of 0.76% by weight and a viscosity of about 260 mPa·s (at 25° C.). When the reaction is complete, the neutral reaction mixture is acidified with 10% strength HCl, the ethyl acetate phase is separated off, and the mixture is concentrated by evaporation. This gives the α,ω-(2-carboxyethyl)-modified polydimethylsiloxane as a virtually colorless, clear oil with a carboxy group content of 2.02% by weight.

EXAMPLE 7 laterally 2-carboxyethyl-modified polydimethylsiloxane

The reaction takes place analogously to Example 1 using a polysiloxane consisting of trimethylsiloxy, dimethylsiloxy and (3-hydroxypropyl)methylsiloxy units with a carbinol group content of 0.37% by weight and a viscosity of about 650 mPa·s (at 25° C.). When the reaction is complete, the neutral reaction mixture is acidified with 10% strength HCl, the ethyl acetate phase is separated off, and the mixture is concentrated by evaporation. This gives the α,ω-(2-carboxyethyl)-modified polydimethylsiloxane as a virtually colorless, clear oil with a carboxy group content of 0.98% by weight.

We claim:

1. A method for preparing organosilicon compounds (2) containing carboxy radicals, and comprising units of the formula $$A_a R_b X_c H_d SiO_{(4-a-b-c-d)/2} \quad (III),$$

where each A is identical or different and is a radical of the formula

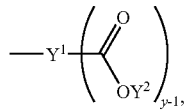  (IV)

by oxidizing organosilicon compounds (1) comprising carbinol radicals and units of the formula $$A'_a R_b X_c H_d SiO_{(4-a-b-c-d)/2}$$  (I), where each A' is identical or different and is a radical of the formula

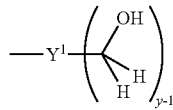

where $Y^1$ is a di- or polyvalent, linear or cyclic, branched or unbranched organic radical optionally substituted and/or interrupted by groups comprising at least one of the atoms N, O, P, B, Si or S, $Y^2$ independently is a hydrogen atom, an organic or inorganic cation, or a monovalent optionally substituted hydrocarbon radical optionally interrupted by heteroatoms, y corresponds to the valency of radical $Y^1$ and is $\geq 2$, R each is identical or different and is a monovalent, SiC-bonded optionally substituted hydrocarbon radical, X each is identical or different and is a chlorine atom, the group A' or a radical of the formula $OR^1$, where $R^1$ is a hydrogen atom or a monovalent optionally substituted hydrocarbon radical optionally interrupted by heteroatoms, a is 0, 1 or 2, b is 0, 1, 2 or 3, c is 0, 1, 2 or 3, and d is 0, 1, 2 or 3, with the proviso that the sum a+b+c+d is $\leq 4$ and the organosilicon compound of the formula (I) has at least one radical A' per molecule and the organosilicon compound of the formula (III) has at least one radical A per molecule;

in the presence of a mediator (3) comprising at least one nitroxyl radical of the formulae

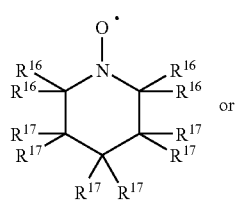  (XI)

or

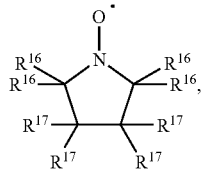  (XII)

where $R^{16}$ each is identical or different and is a phenyl, aryl-$C_1$-$C_5$-alkyl, $C_1$-$C_{12}$-alkyl, $C_1$-$C_5$-alkoxy, $C_1$-$C_{10}$-carbonyl-$C_1$-$C_6$-alkyl radical, where the phenyl radicals are unsubstituted or mono- or polysubstituted by a radical $R^{18}$, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals may be saturated or unsaturated, branched or unbranched and may be mono- or polysubstituted by a radical $R^{18}$, where $R^{18}$ each is identical or different and is a hydroxy, formyl, or carboxy radical, an ester or salt of a carboxy radical, or a carbamoyl, sulfono, sulfamoyl, nitro, nitroso, amino, phenyl, benzoyl, $C_1$-$C_5$-alkyl, $C_1C_5$-alkoxy radical, or $C_1$-$C_5$-alkylcarbonyl radical, $R^{17}$ each is identical or different and is a hydrogen atom or hydroxy, mercapto, formyl, cyano, carbamoyl, carboxy radical, ester or salt of a carboxy radical, sulfono radical, ester or salt of a sulfono radical, sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical, phospho, phosphono, phosphonooxy radical, or ester or salt of a phosphonooxy radical, where the carbamoyl, sulfamoyl, amino, mercapto and phenyl radicals are unsubstituted or mono- or polysubstituted by a radical $R^{12}$, and the aryl-$C_1$-$C_5$-alkyl, $C_1$-$C_{12}$-alkyl, $C_1$-$C_5$alkoxy, $C_1$-$C_{10}$-carbonyl and carbonyl-$C_1$-$C_6$-alkyl radicals are saturated or unsaturated, branched or unbranched and are optionally mono- or polysubstituted by a radical $R^{12}$, and a [—$CR^{17}R^{17}$—] group are optionally replaced by oxygen, an optionally $C_1$-$C_5$-alkyl-substituted imino radical, a (hydroxy)imino radical, a carbonyl function or a vinylidene function optionally mono- or disubstituted by $R^{12}$, and two adjacent groups [—$CR^{17}R^{17}$—] are optionally replaced by a group [—$CR^{17=CR17}$—], [—$CR^{17}$=N—] or [$CR^{17}$=N(O)], where $R^{12}$ each is identical or different and is a hydroxy, formyl, cyano, or carboxy radical, an ester or salt of a carboxy radical, a carbamoyl, sulfono, sulfamoyl, nitro, nitroso, amino, phenyl, C1-C5-alkyl, C1-C5-alkoxy, C1-C5-alkylcarbonyl radical, H—N—OH and at least one oxidizing agent (4), selected from the group consisting of air, oxygen, hydrogen peroxide, organic peroxides, perborates, persulfates, organic and inorganic peracids, salts and derivatives of the peracids, chlorine, bromine, iodine, hypohalic acids and salts thereof, halic acids and salts thereof, halogen acids and salts thereof, $Fe(CN)^{3-}_6$ N-chloro compounds, metal oxides, and anodes of an electrolysis cell, optionally in combination with enzymes, with the proviso that the reaction is carried out while controlling the pH to a pH$\geq 3$, and thereby obtaining an organosilicon compound (2) containing carboxy groups.

2. The method of claim 1, wherein when the reaction is complete, the reaction mixture is acidified to a pH of $\leq 3$ using acids whose $pK_a$ value is less than the $pK_a$ value of the carboxy group in the organosilicon compounds (2) comprising carboxy radicals, and the organosilicon compounds (2) comprising carboxy radicals are obtained in the form of their free acids.

3. The method of claim 1, wherein the organosilicon compounds (1) comprising carbinol radicals have a formula $$A'_v R_w X_{(3-v-w)} Si \quad (I'),$$

where
v is 0, 1, 2 or 3,
w is 0, 1, 2 or 3,
with the proviso that at least one radical A' is present.

4. The method of claim 1, wherein the organosilicon compounds (1) comprising carbinol radicals have a formula $$A'_v R_{3-v} SiO(SiR_2O)_n(SiRA'O)_o SiR_{3-v} A'_v \quad (I''),$$

where
v is 0, 1, 2 or 3,
n is 0 or an integer from 1 to 2000,
o is 0 or an integer from 1 to 2000,
with the proviso that at least one radical A' is present per molecule.

5. The method of claim 4, wherein v is 0 or 1 and o is 0 to 500.

6. The method of claim 1, wherein the organosilicon compounds (1) comprising carbinol radicals have the formula $$[A'_v R_{3-v} SiO_{1/2}]_s [SiO_{4/2}] \quad (I'''),$$

where
v is 0, 1, 2 or 3,
s can assume a value of from 0.2 to 6, inclusive and describes the number of M units $[A'_v R_{3-v} SiO_{1/2}]$, per Q unit $[SiO_{4/2}]$,
with the proviso that at least one radical A' per molecule is present.

7. The method of claim 6, wherein v is 0 or 1 and s is 0.4 to 4 inclusive.

8. The method of claim 1, wherein the organosilicon compounds (2) comprising carboxyl radicals obtained are those of the formula $$A_v R_w X_{(3-v-w)} Si \quad (III'),$$

where
v is 0, 1, 2 or 3,
w is 0, 1, 2 or 3,
with the proviso that at least one radical A is present.

9. The method of claim 8, wherein v is 0 or 1.

10. The method of claim 1, wherein the organosilicon compounds (2) comprising carboxyl radicals obtained are those of the formula $$A_v R_{3-v} SiO(SiR_2O)_n(SiRAO)_o SiR_{3-v} A_v \quad (III''),$$

where
v is 0, 1, 2 or 3,
n is 0 or an integer from 1 to 2000,
o is 0 or an integer from 1 to 2000,
with the proviso that at least one radical A is present.

11. The method of claim 1, wherein the organosilicon compounds (2) comprising carboxyl radicals obtained are those of the formula $$[A_v R_{3-v} SiO_{1/2}]_s [SiO_{4/2}] \quad (III''')$$

where
v is 0, 1, 2 or 3,
s can assume a value of from 0.2 to 6 inclusive and describes the number of M units $[A_v R_{3-v} SiO_{1/2}]$ per Q unit $[SiO_{4/2}]$,
with the proviso that at least one radical A is present.

12. The method of claim 1, wherein the nitroxyl radicals of the formulae (XI) and (XII) are linked to a polymeric structure via one or more radicals $R^{17}$.

13. The method of claim 1, wherein at least one mediator (3) is selected from the group consisting of 2,2,6,6-tetramethylpiperidin-1-oxyl (TEMPO), 4-hydroxy-2,2,6,6-tetramethylpiperidin-1-oxyl, 4-acetamido-2,2,6,6-tetramethylpiperidin-1-oxyl, 4-acetoxy-2,2,6,6-tetramethylpiperidin-1-oxyl, 4-benzoyloxy-2,2,6,6-tetramethylpiperidin-1-oxyl and PIPO (polymer immobilized piperidinyloxyl).

14. The method of claim 1, wherein the mediator (3) is present in an amount of from 0.01 to 100 mol %, based on the amount of carbinol groups present in the organosilicon compound.

15. The method of claim 1, wherein at least one oxidizing agent comprises bleaching liquor.

16. The method of claim 1, wherein the oxidizing agent (4), if it is a 2-electron oxidizing agent, is used in amounts of from 0.2 to 250 mol %, and if it is a 1-electron oxidizing agent, in amounts of from 0.4 to 500 mol %, in each case based on the molar amount of the carbinol groups present in the organosilicon compounds.

17. The method of claim 1, wherein the method is carried out continuously.

* * * * *

UNITED STATES PATENT AND TRADEMARK OFFICE
CERTIFICATE OF CORRECTION

PATENT NO. : 7,902,392 B2  Page 1 of 1
APPLICATION NO. : 11/568050
DATED : March 8, 2011
INVENTOR(S) : Christian Ochs It is certified that error appears in the above-identified patent and that said Letters Patent is hereby corrected as shown below:

Column 18, Lines 52-53, Claim 1:

Delete "C1-C5-alkyl, C1-C5-alkoxy, C1-C5-alkylcarbonyl radical" and
Insert -- $C_1$-$C_5$-alkyl, $C_1$-$C_5$-alkoxy, $C_1$-$C_5$-alkylcarbonyl radical --.

Column 18, Line 54, Claim 1:

Delete "H—N—OH"

Signed and Sealed this
Twenty-fourth Day of July, 2012

David J. Kappos
*Director of the United States Patent and Trademark Office*